United States Patent [19]

Hobson et al.

[11] Patent Number: 4,836,219

[45] Date of Patent: Jun. 6, 1989

[54] ELECTRONIC SLEEP MONITOR HEADGEAR

[75] Inventors: J. Allan Hobson, Brookline; Adam Mamelak, Boston; Rita Helfand, Cambridge, all of Mass.; Peretz Lavie, Haifa, Israel

[73] Assignee: President & Fellows of Harvard College, Cambridge, Mass.

[21] Appl. No.: 70,988

[22] Filed: Jul. 8, 1987

[51] Int. Cl.[4] .............................................. A61B 5/10
[52] U.S. Cl. .................................... 128/782; 340/575; 340/576
[58] Field of Search ....................... 128/774, 782, 733; 340/573, 575–576

[56] References Cited

U.S. PATENT DOCUMENTS

| | | | |
|---|---|---|---|
| 3,363,242 | 1/1968 | Currey et al. | 128/782 X |
| 3,658,054 | 4/1972 | Iberall | 128/672 |
| 4,272,764 | 6/1981 | Herr et al. | 340/576 X |
| 4,359,724 | 11/1982 | Zimmerman et al. | 128/733 X |

FOREIGN PATENT DOCUMENTS

| | | | |
|---|---|---|---|
| 3102239 | 8/1982 | Fed. Rep. of Germany | 128/733 |
| 1534545 | 7/1968 | France | 128/782 |

OTHER PUBLICATIONS

Thomas et al., "Transducer for Recording Fine Eye Movement Through the Closed Eyelid"; Med. and Biol. Engr. and Comput., vol. 15, No. 6, 11-1977, pp. 705-706.
Industrial Research Prod. Annual, 9-1973, p. 47.
Aaronson et al. (1982) Arch. Gen. Psychiatry 39:330-335.
Kayed et al. (1979) Sleep 2(2):253-260.
Hobson et al. (1978) Science 201:1251-1255.
Helfand et al. (1986) Psychophysiology 23(3):334-339.

Primary Examiner—Lyle L. Howell
Assistant Examiner—Angela D. Sykes

[57] ABSTRACT

Electronic filters are applied to analog signals representative of eye movement and head movement, obtained from detectors attached to a simple headgear, to provide satisfactory information for automatically reporting an individual's sleep state. The filters determine whether there has been substantial eye and head movement in a given period. Each filter then generates binary output signals representing movement (or the absence of it). Noise filters and a comparison filter are then applied to the binary output signals to predict sleep state; REM sleep; NREM sleep; or wakefulness.

20 Claims, 2 Drawing Sheets

ELECTRONIC SLEEP MONITOR HEADGEAR

BACKGROUND OF THE INVENTION

This invention relates to sleep monitors, used e.g., in therapy, diagnosis, or research, which differentiate various sleep and wakeful states.

Normal individuals experience distinct sleep states. One important sleep state, REM sleep, is characterized by rapid eye movements, small muscle twitches, and the absence of other body movements. The other sleep state, non-REM (NREM) sleep is subdivided into four grades or states (I-IV), stage I being the most shallow (least restful or refreshing) and stage IV being the deepest.

Monitoring and individual's sleep state is important for diagnosising sleep disorders. It is also important for diagnosising and following response to treatment of depression (affective disorder) in which REM latency is significantly reduced.

It is estimated that 8-15% of the adult U.S. population have frequent complaints about sleep quality and quantity, and 3-11% use sedative hypnotic drugs for these complaints. Sleep disorders can be debilitating. They are expensive and difficult to diagnose and treat. For diagnosis, the patient's sleep state may be monitored to determine the pattern and duration of various sleep states. Sleep is qualitatively and quantitatively evaluated by measuring the electrical signals produced by brain and muscle activity, using electrophysiological techniques and instruments. A widely used technique for this purpose (described in Rechtshaffen and Kales, eds., *A Manual of Standardized Terminology, Techniques, and Scoring System For Sleep Stages of Human Subjects*, Wash. D.C. U.S. Gov't. Print Off. Public Health Service) involves simultaneously and continuously measuring electroencephalographic (EEG) data—signals derived primarily from the cortex of the brain and sometimes referred to as an electrocortigram (ECoG)—along with an electromyogram (EMG) signal which monitors muscle activity, generally from one of the muscles of the lower jaw, together with left- and right-eye electrooculogram (EOG) signals produced by eye movement. These EEG, EMG, and EOG signals are conventionally recorded on a multi-channel physiological recorder (sometimes referred to as a polysomnograph). A skilled technician, using standardized criteria for evaluating such recordings, grades each period of the recording as awake, NREM state I to IV sleep, or REM sleep, to produce a sleep profile of the type of sleep as a function of time. The technician will then determine the proportion of the total sleep period spent in each of the grades of NREM sleep and in REM sleep.

The above method, which is the "standard" in sleep research, usually involves the use of a large number of (e.g. ten) electrodes pasted and taped to the subject's body. These electrodes and the wires connecting them to the polygraph recorder cause discomfort and restricted movement. It can be difficult to obtain a time series study on a subject because of the discomfort involved from the associated measurement apparatus.

The above method also requires costly equipment and skilled labor. A standard sleep investigation can cost in the neighborhood of $1000 per night, and it can last for several nights. There may be long waiting lists for sleep evaluation labs.

In view of the difficulties with existing sleep evaluation techniques, many patients who present with sleep disorders are not tested with those techniques, and are treated with sedative-hypnotic drugs without detailed evaluation.

Photographic techniques also have been used to evaluate sleep state. Hobson et al. (1978) *Science* 201: 1251–1255 measured the mobility of sleeping subjects photographically and predicted transitions between NREM and REM on the premise that major body posture shifts occur immediately preceeding and following REM sleep. Hobson et al. suggest that " . . . [P]ostural immobility, easily detectable in time lapse photographic data, could by itself provide a simple quantitative readout of the state of the brain oscillator controlling the REM-NREM sleep cycle." Time lapse photography is suggested as a means of conducting field studies of sleep behavior.

Aaronson et al. (1982) *Arch. Gen. Psychiatry* 39: 330–335 report the use of time-lapse video recording to monitor sleep state, based on the knowledge that major body movements are known to occur predominantly before and after recurrent episodes of REM sleep, and the longest periods of immobility are associated with non-REM episodes. Sleep latency and REM onset were predicted from such major movements. Evidence of small body movement specific to REM sleep was also observed.

Kayed et al. (1979) *Sleep* 2 (2): 253–260 disclose an antioculographic sleep monitor (AOGM) system for recording eye movement, body movements and electromyogram (EMG) signals to monitor muscle activity. In addition to the EMG signal, the system includes a piezo-ceramic transducer attached to the eyelid to sense eye movements and a second transducer attached to an index finger joint to sense body movement. Analog signals from each of the sensors are recorded on tape, and the tapes are analyzed and scored by standard criteria. At p. 260, Kayed et al. say, "The introduction of miniature transducers that can be applied directly on the eyelid provides an easy method for recording eye and body movements and makes simultaneous eye and body movement monitoring possible. The various combinations of these two parameters await further attention, and the study of their temporal relationships may provide interesting information to sleep phenomenology. The use of submental EMG helps to confirm the transition from non-REM to REM; however, further experience may prove that its use is not mandatory."

SUMMARY OF THE INVENTION

We have obtained satisfactory information for automatically (e.g., computer generated without technician intervention) reporting the sleep state of an individual subject of applying an electronic filter to analog signals representative of eye movement. The filter receives the analog signal and produces a binary output signal having two values, one representing substantial movement, and the other representing the absence of substantial movement. Additional filtering of this output signal permits designation of time periods of predetermined duration as eye-movement periods or non-eye-movement periods. In this way, a simple eye movement detector can be combined with the above described electronic filters to provide reliable discrimination between REM and NREM sleep.

Accordingly, the invention generally features apparatus for reporting an individual's sleep state comprising:

(a) means responsive to an individual's eye movement generating an analog signal; (b) means responsive to the analog signal to generate an output signal having a first value during substantial eye movement and a second value during the absence of substantial eye movement; and (c) means responsive to the output signal for designating a time period of predetermined duration as an eye-movement period of a non-eye-movement period.

Preferably, to avoid designating wake periods as REM, the apparatus includes means responsive to the individual's body movements for generating a second analog signal, and means responsive to the second analog signal to designate periods of substantial body movement as non-eye-movement periods.

For more sophisticated sleep state reports that differentiate between wake, REM and NREM, the body-movement detector is connected to means responsive to the second analog signal for generating a second output signal having a first value during substantial body movement and a second value during the absence of substantial body movement. The apparatus also includes means to designate predetermined periods as body-movement or non-body-movement periods, responsive to the second output signal. An electronic signal representative of sleep state (wake, REM or NREM) is produced responsive to both the first and the second output signals using electronic storage means for providing reference signals representative of criteria for designating sleep state, and means for comparing those reference signals to the first output signal value and to the second output signal value. Preferably the first and second output signals are filtered by means for counting the number of times each of the output signals switches from its first value to its second value, and comparing that number to threshold eye-movement and head-movement frequencies, respectively.

The above apparatus is particularly well suited for simple, inexpensively produced, non-invasive head gear, which contains at least some of the electronic circuitry described above, and which has the body-movement sensor mounted on it. The eye-movement sensor is attached to the head gear circuitry, so there is no need for any additional equipment or electrical attachments to the subject. One headgear design includes a sweat band extending circumferentially around the head and a crossband on which the head-movement sensor is mounted.

A second aspect of the invention features automatically determining the sleep state of an individual by generating a first analog electrical signal responsive to the individual's eye movement and, responsive to that signal, producing a first output electrical signal having a first value during substantial eye movement and a second value in the absence of substantial eye movement. Responsive to the output signal, time periods of predetermined duration are successively designated as eye-movement periods or non-eye-movement periods.

In preferred embodiments of the method, a second analog signal representative of body movement is generated as described above and used to designate predetermined time periods as body-movement or non-body-movement periods. Specifically, the analog signals may be filtered as described above to determine whether they exceed predetermined threshold values a predetermined number of times in the time period.

The invention thus enables an effective lightweight, unobtrusive, automatic sleep state indicator, that does not require subjective operator evaluation and does not involve EMG measurement.

Other features and advantages of the invention will be apparent from the following description of preferred embodiments and from the claims.

DESCRIPTION OF THE PREFERRED EMBODIMENT

We first briefly describe the figures of a preferred embodiment of the invention.

Figures

APPARATUS

Figure 1:
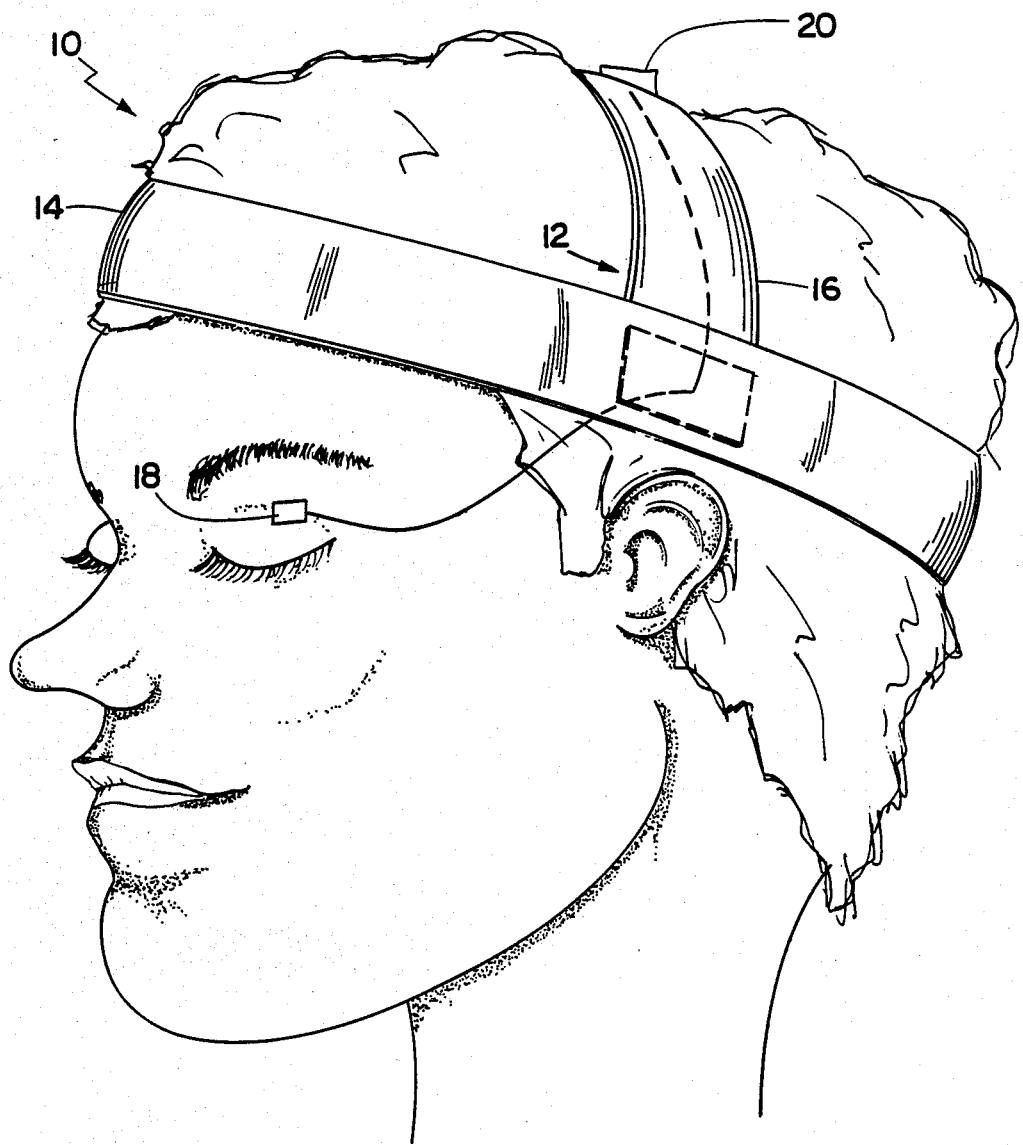
FIG. 1 is a highly diagrammatic view of a headband for reporting an individual's sleep state.

In FIG. 1, the sleep state reporting apparatus 10 is fixed in place by headband 12 consisting of circumferential elastic band 14, such as an athletic sweatband, and transverse elastic band 16.

Apparatus 10 includes two movement sensors 18 and 20: Eye-movement sensor 18, e.g. a semiconductor strain gauge or a piezo-electric film gauge such as those available from Penwalt Co., Valley Forge, PA, is attached to the eyelid with adhesive tape. Head-movement sensor 20 is positioned on the middle of transverse band 16. Sensor 20 is a piezo-ceramic phonograph crystal fixed between layers of headgear band 16.

Figure 2:
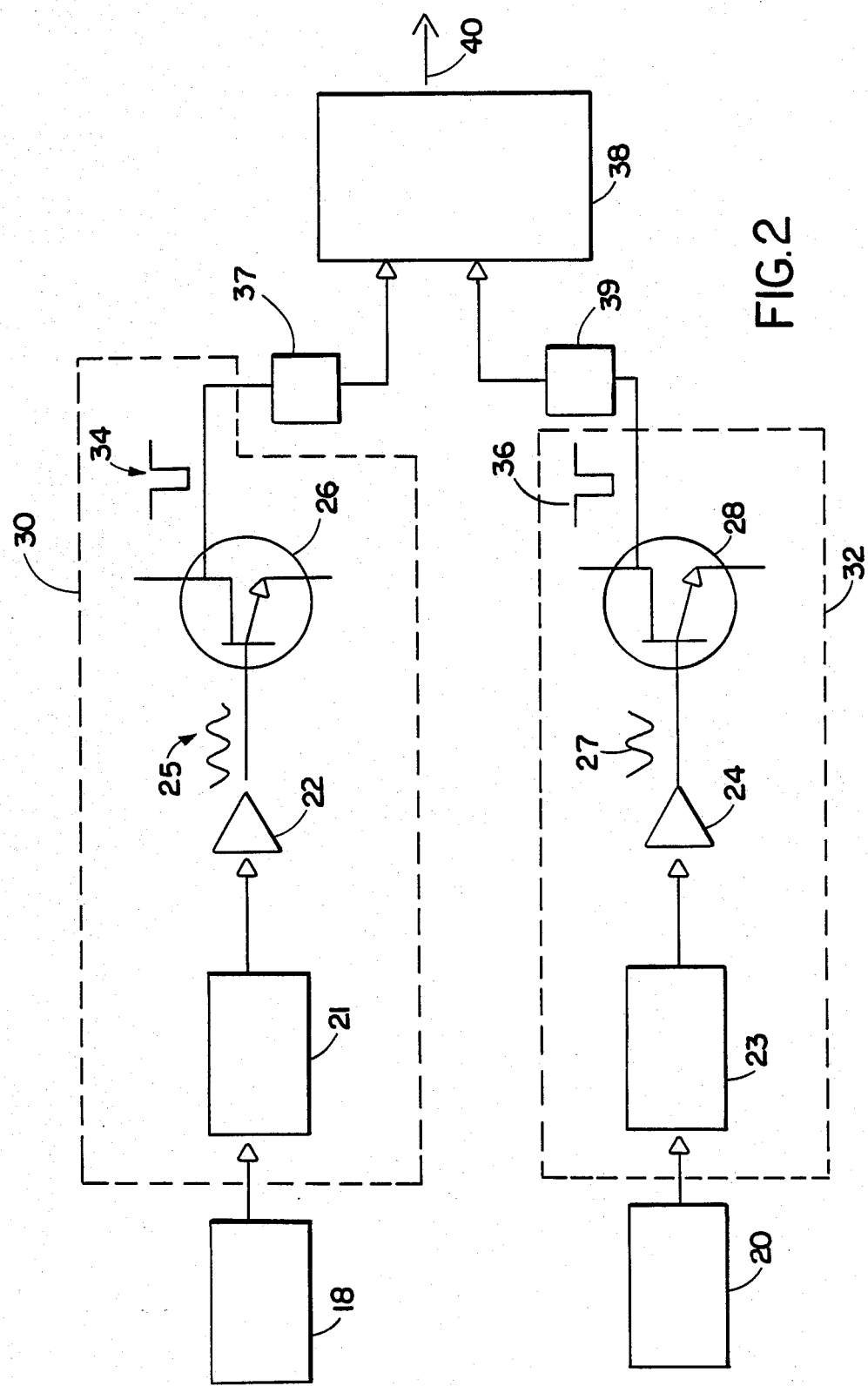
FIG. 2 is a diagram of electronic circuitry used in the headgear of FIG. 1.

Some or all of the electronic circuitry 30 and 32 shown in FIG. 2 may be positioned within head band 10. As shown in FIG. 2, sensors 18 and 20 produce two distinct analog electric signals representative of eye movement and head movement respectively. The signals are filtered by low pass filters 21 and 23 to remove extraneous signals having frequencies above 5 Hz. The signals are then amplified by standard operational amplifiers 22 and 24, respectively, yielding signals 25 and 27, respectively which are then filtered by filters 26 and 28, respectively.

Filter 26 consists of a transistor which converts analog signals above a certain threshold (e.g. 0.3 volts) to a digital signal 34 ignoring analog values below that threshold; filter 28 consists of a transistor which also converts along signals above a certain threshold (e.g. 0.2 volts) to a second digital signal 36, ignoring analog values below that threshold.

Digital signals 34 and 36 are input to noise filters 37 and 39 and then to an electric comparison filter 38 (also called a sleep state predictor) which compares digital movement reports to predetermined criteria indicative of sleep states. Comparison filter 38 can be a computer (e.g. a personal computer) with a suitable software program to perform operations, described below or it can be an electronic circuit containing a ROM, committed to make those operations. In designing filters 37, 38, and 39:

(a) a sample period is selected to determine the existence of movement;

(b) a filter is established to determine the number of digital signals required in the sampling period to designate the period as positive for movement;

(c) a sleep-state predictor is established to determine sleep state based on the movement pattern represented by the digital signals.

Filters 37 and 39 are designed so that a minimum of between 0 and 5 signals per period (30–90 seconds, preferably 60 seconds) are required to designate the period as a period of movement. The value selected for this filter varies from subject to subject, for example for light sleepers versus heavy sleepers, but that value remains relatively constant for a given subject from night to night. Comparison filter 38 is designed to recognize the following general principles: head movement of prolonged duration (greater than three minutes) indicates wakefulness; lack of head and eye movement indicate NREM sleep; and eye movement alone indicates REM sleep. Specifically, the comparison filter is set so that:

(a) if subject is in a wake state, if a certain number (3-8) of consecutive periods substantially lacking in both eye and head movement, an output signal indicating change to NREM is generated;

(b) if subject is in NREM, an output signal indicating change to REM is generated if a certain number (2-4) of consecutive periods of substantial eye movement which are substantially lacking in head movement;

(c) if subject is in NREM or REM, an output signal indicating wake is generated if a certain number (2-5) of consecutive periods of substantial head movement;

(d) if subject is in REM, an output signal indicating NREM is generated if a certain number (4-7) of consecutive period substantially lacking in eye movement.

As diagrammed in FIG. 2, there is a hard-wire connection to transmit signals to filter 38. Other systems such as radio transmission or storage/read out systems can also be used.

The output 40 from filter 38 is a signal indicating sleep state, e.g., a light panel or a chart recorder, or storage in electronic memory.

The above-described filters and sleep-state predictor are highly accurate, and they avoid the need for costly, time-consuming and subjective scoring by individual researchers. It is convenient to use head movement as a measure of body movement, so that the entire apparatus can be contained in a single headgear, without remote sensing of outer body movements. There is no need to use EMG signals.

It is particularly significant and surprising that, predictions based on both eye and head movement, filtered as described above, provide satisfactory information as to sleep state. It is also significant and surprising that EOG recorded eye movement is unnecessary; the eye transducer responds to eyelid stretching from corneal movement or from blinking. The eye transducer is sensitive to small movements and clearly differentiates REM eye movements showing a much higher intensity of movement peaks during REM as opposed to NREM sleep.

Operation

In operation, the first sleep session may be used to calibrate the filters. Specifically, to calibrate noise filter 37, the number of digital signals 34 and 36 in a selected time period is plotted as a histogram, to determine the mode of signal frequency. Noise filter 37 is calibrated to treat period with fewer signals than the mode as non-movement periods. Alternatively, after the first session, the modes of signal frequency can be electronically determined, and the sleep state can be reported automatically as described above, using electronically determined mode values.

Such calibration is successful because surprisingly, while there is some variation from subject to subject (some people are more active sleepers than others), variations from night to night for a given subject are not severe.

After calibration, the subject is fitted comfortably with the headgear, e.g. using velcro tabs for adjustability, and sleep state is monitored as described above.

Other Embodiments

Other embodiments are within the following claims. For example, the physical location of noise filter 37 and comparison filter 38 can vary, as can the timing of performance of those functions. For example, digital signals can be stored in a storage microchip, that is fixed on the headband. When the sleep session ends, the stored information is transmitted to a remote location having (optically) filters and a computer programmed with appropriate software to perform the desired functions. The signals can be transmitted by a micro transmitter.

Particularly for sound sleepers, it has been found that the middle of a REM period occasionally may be scored as NREM; to avoid this problem, when two shifts to REM are indicated within a given short period (e.g. 10 minutes or less), the intervening period may be scored as REM, by retrospectively canceling the intervening indication of a change out of REM.

We claim:

1. Apparatus for reporting an individual's sleep state comprising:
   (a) means responsive to the individual's eye movement generating a first analog signal;
   (b) means responsive to the first analog signal for producing a first output signal having a first value during substantial eye movement and a second value in the absence of substantial eye movement;
   (c) means responsive to said first output signal value for designating a time period of predetermined duration as an eye-movement period or a non-eye-movement period;
   (d) means responsive to body movements of said individual for generating a second analog signal;
   (e) means responsive to said second analog signal for producing a second output signal having a first value during substantial body movement and a second value in the absence of substantial body movement;
   (f) means responsive to said second output signal for designating a time period of predetermined duration as a body-movement period or a non-body-movement period; and
   (g) means responsive both to the eye-movement period designation and the body-movement period designation for producing an electronic signal representative of sleep state.

2. The apparatus of claim 1 wheren said means (g) comprises electronic storage means for providing reference electronic signals representative of criteria for designating sleep state, and means for comparing said reference signals to said first output signal value and to said second output signal value.

3. The apparatus of claim 2 wherein said means (c) comprises a first filter means for detecting the number of times said first output signal switches from its first value to said second value during the time period and for comparing said number to a threshold eye-movement frequency,
   whereby the first filter means indicates the presence or absence of substantial eye movement in the time period.

4. The apparatus of claim 3 wherein said means (e) comprises a second filter means for detecting the number of times said second output signal switches from its first value to its second value during the time period and for comparing that number to a threshold body-movement frequency, whereby said second filter means indicates the presence or absence of substantial body movement in the time period.

5. The apparatus of claim 4 wherein said apparatus comprises clock means to store said period said stored period being between 20 seconds and 90 seconds.

6. The apparatus of claim 5 wherein said apparatus comprises means to store said threshold eye-movement frequency, said stored threshold eye-movement frequency being between 0 and 5 movements per minute.

7. The apparatus of claim 5 wherein said apparatus comprises means to store said threshold body-movement frequency, said stored threshold body-movement frequency being between 0 and 5 movements per minute.

8. The apparatus of claim 4 wherein means (g) comprises means responsive to said first filter and to said second filter means for changing said electronic signal representative of sleep state to indicate change from:

(i) wake to NREM if said first filter means indicates the absence of substantial eye movement and said second filter means indicates the absence of substantial body movement in a predetermined consecutive number W of said time periods;

(ii) wake or NREM or REM if said first filter means indicates the presence of substantial eye movement and said second filter means indicates the absence of substantial body movement in a predetermined consecutive number X of said time periods;

(iii) NREM or REM to wake if said second filter indicates the presence of substantial body movement in a predetermined consecutive number Y of said time periods;

(iv) REM to NREM if said first filter means indicates the absence of substantial eye movement in a predetermined consecutive number Z of said time periods.

9. The apparatus of claim 8 wherein said apparatus comprises means to store W at a value of $3 \leq W \leq 8$.

10. The apparatus of claim 8 wherein said apparatus comprises means to store X at a value of $2 \leq X \leq 4$.

11. The apparatus means to store Y at a value of $2 \leq Y \leq 5$.

12. The apparatus of claim 8 wherein said apparatus comprises means to the Z at a value of $4 \leq Z \leq 7$.

13. The apparatus of claim 8 wherein said means (g) further comprises means to retrospectively cancel the indication of change from REM to NREM, if said means responsive to said first filter means and to said second filter means indicates a subsequent return to REM within a predetermined number Q of said time periods after said indication of change from REM to NREM.

14. The apparatus of claim 1 further comprising headgear, at least one of said means (d) and said means (e) being affixed to the headgear, and said means (d) being responsive to head movements of said individual.

15. The apparatus of claim 14 wherein said headgear comprises a first band extending circumferentially around the head and second band connecting opposite sides of said first band across the top of the head.

16. The apparatus of claim 15 wherein said means (d) is positioned on said second band.

17. A method of automatically determined the sleep state of an individual comprising:

generating a first analog electric signal responsive to the individual's eye movement;

responsive to the first analog signal, producing a first output electric signal having a first value during substantial eye movement a second value in the absence of substantial eye movement;

responsive to said first output electrical signal, designating a time period of predetermined duration as an eye-movement period or a non-eye movement period;

generating a second analog signal representative of body movement; and responsive to said second analog signal, generating a second output signal having a first value during substantial body movement and a second value in the absence of substantial body movement.

18. The method of claim 17 wherein said time period is designated as an eye-movement period if said first analog signal exceeds a predetermined threshold value at least a predetermined number of times in said period.

19. The method of claim 18 further comprising:

(a) selecting a first analog threshold value for said first analog electric signal;

(b) selecting a second analog threshold value for said second analog electric signal;

(c) selecting a time period for counting peaks in said first analog signal and in said second analog signal; and (d) determining whether the number of first analog signal peaks in said time period exceeds said first threshold, and, if so, generating said first output signal at said first value and, if not; generating said first output signal at said second value;

(e) determining whether the number of second analog signal peaks in said time period exceeds said second threshold, and, if so, generating said second output signal at said first value and, if not, generating said second output signal at said second value.

20. The method of claim 19 comprising comparing the first output signal and the second output signal to stored information, and generating a sleep state signal representative of change in a sleep state as follows:

(a) wake to NREM if said comparison indicates the absence of substantial eye movement and the absence of substantial body movement in a predetermined consecutive number of W of said time periods;

(b) wake or NREM to REM if said comparison indicates the presence of substantial eye movement and the absence of substantial body movement in a predetermined consecutive number X of said time periods;

(c) NREM or REM to wake if said comparison indicates the presence of substantial bread movement in a predetermined consecutive number Y of said time periods;

(d) REM to NREM if said comparison indicates the absence of substantial eye movement in a predetermined consecutive number Z of said time periods.

* * * * *